US012629666B2

(12) United States Patent
Yokoi et al.

(10) Patent No.: US 12,629,666 B2
(45) Date of Patent: May 19, 2026

(54) CATALYSTS COMPRISING PHOSPHORUS STABILIZED MSE FRAMEWORK TYPE ZEOLITE, ITS PREPARATION AND USE THEREOF IN FLUID CATALYTIC APPLICATIONS

(71) Applicant: BASF CORPORATION, Florham Park, NJ (US)

(72) Inventors: Toshiyuki Yokoi, Tokyo (JP); Bilge Yilmaz, Iselin, NJ (US); Chandrashekhar Kelkar, Iselin, NJ (US); Sungsik Park, Tokyo (JP); Christopher John Gilbert, Iselin, NJ (US)

(73) Assignee: BASF CORPORATION, Florham Park, NJ (US)

( * ) Notice: Subject to any disclaimer, the term of this patent is extended or adjusted under 35 U.S.C. 154(b) by 0 days.

(21) Appl. No.: 18/033,972

(22) PCT Filed: Nov. 3, 2021

(86) PCT No.: PCT/US2021/057919
§ 371 (c)(1),
(2) Date: Apr. 26, 2023

(87) PCT Pub. No.: WO2022/098773
PCT Pub. Date: May 12, 2022

(65) Prior Publication Data

US 2024/0416331 A1 Dec. 19, 2024

Related U.S. Application Data

(60) Provisional application No. 63/109,414, filed on Nov. 4, 2020.

(51) Int. Cl.

| | |
|---|---|
| ***B01J 29/80*** | (2006.01) |
| ***B01J 29/08*** | (2006.01) |

(Continued)

(52) U.S. Cl.
CPC ............. *B01J 29/80* (2013.01); *B01J 29/084* (2013.01); *B01J 29/40* (2013.01); *B01J 29/70* (2013.01);
(Continued)

(58) Field of Classification Search
None
See application file for complete search history.

(56) References Cited

U.S. PATENT DOCUMENTS

| | | | | |
|---|---|---|---|---|
| 6,080,303 A | 6/2000 | Cao et al. | | |
| 7,198,711 B1 * | 4/2007 | Chester | ................ | C07D 487/08 585/446 |

(Continued)

FOREIGN PATENT DOCUMENTS

| | | |
|---|---|---|
| JP | 2013-039549 A | 2/2013 |
| JP | 2017-088597 A | 5/2017 |

(Continued)

OTHER PUBLICATIONS

International Search Report of International Application No. PCT/US2021/057919 mailed Feb. 10, 2022, 13 pgs.

(Continued)

*Primary Examiner* — Ali Z Fadhel
(74) *Attorney, Agent, or Firm* — Peter DiMauro

(57) ABSTRACT

Disclosed herein is a catalyst component suitable for petroleum refining applications (e.g., fluid catalytic cracking and hydrocracking) that includes a MSB zeolite structure (e.g., MCM-68) and a non-zeolitic matrix. The first component may be combined with additional components into a catalyst composition. Also disclosed herein are methods of preparing the catalyst component and/or catalyst compositions as well as method of using the catalyst component and/or catalyst composition.

17 Claims, 3 Drawing Sheets

(51) Int. Cl.

| | |
|---|---|
| ***B01J 29/40*** | (2006.01) |
| ***B01J 29/70*** | (2006.01) |
| ***B01J 35/61*** | (2024.01) |
| ***B01J 35/63*** | (2024.01) |
| ***B01J 37/00*** | (2006.01) |
| ***B01J 37/02*** | (2006.01) |
| ***B01J 37/10*** | (2006.01) |
| ***B01J 37/28*** | (2006.01) |
| ***C01B 39/02*** | (2006.01) |
| ***C01B 39/48*** | (2006.01) |
| ***C07C 4/06*** | (2006.01) |

(52) U.S. Cl.

CPC ......... *B01J 29/7007* (2013.01); *B01J 35/615* (2024.01); *B01J 35/633* (2024.01); *B01J 37/0018* (2013.01); *B01J 37/0201* (2013.01); *B01J 37/10* (2013.01); *B01J 37/28* (2013.01); *C01B 39/026* (2013.01); *C01B 39/48* (2013.01); *C07C 4/06* (2013.01); *B01J 2229/24* (2013.01); *B01J 2229/36* (2013.01); *C01P 2002/72* (2013.01); *C01P 2006/12* (2013.01); *C01P 2006/14* (2013.01); *C07C 2529/70* (2013.01)

(56) References Cited

U.S. PATENT DOCUMENTS

| | | | | |
|---|---|---|---|---|
| 2013/0115164 | A1 | 5/2013 | Fu et al. | |
| 2018/0169623 | A1* | 6/2018 | Weiss | B01J 29/76 |
| 2020/0392418 | A1* | 12/2020 | Nesterenko | C07C 4/06 |
| 2022/0143586 | A1* | 5/2022 | Beutel | B01J 35/617 |

FOREIGN PATENT DOCUMENTS

| | | | |
|---|---|---|---|
| WO | 2000/43466 | A1 | 1/2000 |
| WO | 2020/190367 | A1 | 9/2020 |

OTHER PUBLICATIONS

Han et al., "Selective Production of Light Olefins over MSE-type Zeolite Catalyst", Journal of the Japan Petroleum Institute, Nov. 1, 2017, vol. 60, No. 6, pp. 288-300.

Kakiuchi et al. "Phosphorus modified small-pore zeolites and their catalytic performances in ethanol conversion and NH3-SCR reactions", Applied Catalysis A: General, Nov. 1, 2017, vol. 575, pp. 204-213.

Park et al. "Selective formation of light olefins from dimethyl ether over MCM-68 modified with phosphate species", Catalysis Today, vol. 265, May 1, 2016, pp. 218-224.

* cited by examiner

CATALYSTS COMPRISING PHOSPHORUS STABILIZED MSE FRAMEWORK TYPE ZEOLITE, ITS PREPARATION AND USE THEREOF IN FLUID CATALYTIC APPLICATIONS

CROSS-REFERENCE TO RELATED APPLICATION(S)

This application claims the benefit of priority of U.S. Provisional Application No. 63/109,414, filed on Nov. 4, 2020, the disclosure of which is hereby incorporated by reference herein in its entirety.

FIELD OF THE DISCLOSURE

The present disclosure relates to petroleum refining catalysts and compositions thereof. In particular, the present disclosure relates to the use of MSE zeolite structures for fluid catalytic cracking (FCC) applications, methods of their preparation, and methods of their use.

BACKGROUND OF THE DISCLOSURE

FCC is the main source of world's butylenes production. Almost half of the butylenes production is sourced from FCC units, and more than 40% of it is consumed to make high octane blending components via alkylation units. Due to increasing demand for improved fuel efficiency, more and more refiners find it profitable to increase butylenes in their units. However, conventional olefin maximization additives based on ZSM-5 alone are not sufficient to meet this target. ZSM-5 additives are designed to make propylene; thus, they make more propylene over butylenes. When the units are wet-gas compressor limited the use of ZSM-5 will increase propylene more than butylenes, thus reaching the liquefied petroleum gas (LPG) limit constraints before reaching the required butylenes yields. In such a scenario the unit needs a catalyst (or additive) solution which contributes to increased butylenes/propylene (C4=/C3=) ratio compared to ZSM-5. Identifying materials with adjusted selectivity toward specific small olefins (e.g., butylenes) in a controlled and deliberate manner is of interest in petroleum refining applications (e.g., fluid catalytic cracking, hydrocracking).

SUMMARY OF THE DISCLOSURE

In certain embodiments, the present disclosure provides a catalyst component that includes a zeolite having a MSE zeolite structure (e.g., MCM-68 zeolite) that has been phosphorus stabilized with about 0.5 wt. % to about 10 wt. % phosphorus, based on the total weight of the zeolite, and a non-zeolitic matrix.

In certain embodiments, the phosphorus content in the catalyst component ranges from about 1 wt. % to about 5 wt. % or from about 2 wt. % to about 4 wt. %, based on total weight of the zeolite.

In certain embodiments, the non-zeolitic matrix includes one or more of clay, alumina, silica, titania, zirconia, magnesia, kaolin, metakaolin, halloysite, kaolinite, dickite, nacrite, anauxite, silica-alumina, silica-magnesia, silica-zirconia, silica-thoria, silica-beryllia, silica-titania, silica-alumina-thoria, silica-alumina-zirconia, silica-alumina-magnesia, silica-magnesia-zirconia, or a mixture thereof.

In certain embodiments, the phosphorus stabilized zeolite having MSE structure (e.g., MCM-68) is present in the catalyst component in an amount of about 1 wt. % to about 90 wt. %, about 2 wt. % to about 80 wt. %, or about 5 wt. % to about 60 wt. %, based on total weight of the catalyst component.

In certain embodiments, the catalyst component has an total acidity of about 0.5 mmol/(g catalyst component).

In certain embodiments, the phosphorus stabilized zeolite having MSE structure (e.g., MCM-68) has a silicon to aluminum ratio (SAR) ranging from about 5 to about 60, from about 7 to about 30, or from about 9 to about 15.

In certain embodiments, the BET total surface area of the catalyst component ranges from about 150 $m^2/g$ to about 750 $m^2/g$, from about 175 $m^2/g$ to about 675 $m^2/g$, or from about 200 $m^2/g$ to about 600 $m^2/g$.

In certain embodiments, the t-plot micropore volume of the catalyst component ranges from about 0.05 cc/g to about 0.3 cc/g, from about 0.06 cc/g to about 0.23 cc/g, or from about 0.07 cc/g to about 0.16 cc/g.

In certain embodiments, the phosphorus stabilized zeolite has an MSE structure including porous crystalline material which contains at least one channel system, in which each channel is defined by a 12-membered ring of tetrahedrally coordinated atoms, and at least two further, independent channel systems, in each of which each channel is defined by a 10-membered ring of tetrahedrally coordinated atoms, wherein the number of unique 10-membered ring channels is twice the number of 12-membered ring channels.

In certain embodiments, the phosphorus stabilized zeolite having MSE structure (e.g., phosphorus stabilized MCM-68) has a first X-Ray Diffraction (XRD) pattern, which is substantially similar, in terms of peaks locations and relative intensity, to a second XRD pattern of that zeolite without phosphorus stabilization (e.g., MCM-68 zeolite without phosphorus).

In certain embodiments, the present disclosure provides a catalyst composition for petroleum refining applications (such as fluid catalytic cracking (FCC) and/or hydrocracking) that includes a first component and a second component.

The first component includes a zeolite having MSE zeolite structure (e.g., MCM-68 zeolite) that has been phosphate stabilized with about 0.5 wt. % to about 10 wt. % phosphorus, based on the total weight of the zeolite in the first component, and a non-zeolitic matrix. The first component can also be any of the catalyst components described herein, which include a zeolite with the MSE zeolite structure.

The second component being compositionally different from the first component. In certain embodiments, the second component includes a second non-zeolitic matrix and one or more zeolites (e.g., ZSM-5, zeolite Y, beta zeolite, and more). In certain embodiments, the catalyst composition may include at least one additional catalyst component that is compositionally different from the first component and from the second component (e.g., ZSM-5, zeolite Y, beta zeolite, and more).

In certain embodiments, the first catalyst component is present in the catalyst composition in an amount ranging from about 1 wt. % to about 25 wt. %, from about 1.5 wt. % to about 15 wt. %, or from about 2 wt. % to about 10 wt. %, based on total weight of the catalyst composition.

In certain embodiments, the second catalyst component and any additional catalyst component if included, are present in the catalyst composition (cumulatively) in an amount ranging from about 75 wt. % to about 99 wt. %, from about 85 wt. % to about 98.5 wt. %, or from about 90 wt. % to about 98 wt. %, based on total weight of the catalyst composition.

In certain embodiments, the instant disclosure is directed to a process for preparing any of the catalyst components described herein, which include a phosphate stabilized zeolite with MSE zeolite structure. In certain embodiments, the process includes stabilizing (e.g., modifying by impregnation for example) the zeolite with MSE zeolite structure (e.g., MCM-68) with a phosphorus containing compound, such as, without limitations, phosphoric acid, diammonium phosphorus, or a combination thereof. In certain embodiments, the process may further include calcining the phosphorus stabilized zeolite with the MSE zeolite structure (e.g., the phosphorus stabilized MCM-68).

In certain embodiments, the instant disclosure is directed to a process for preparing any of the catalyst compositions described herein by combining any of the catalyst components described herein (referred to as first catalyst component), which include a phosphorus stabilized zeolite with MSE zeolite structure, with a second catalyst component that is compositionally different from the first catalyst component, and optionally with at least one additional catalyst component.

The catalyst compositions described herein include multiple zeolitic frameworks to deliver superior butylenes activity, butylenes yield, and butylenes selectivity, while maintaining constant or lower yields and selectivity for less desired products, such as hydrogen, coke, higher hydrocarbons (such as C6 and C7), and lower hydrocarbons (such as C3). The catalyst components described herein, which include a phosphorus stabilized zeolite with MSE zeolite structure, also deliver similar superior performance.

In certain embodiments, the instant disclosure is directed to a process for catalytic cracking of a hydrocarbon feedstock by contacting the feedstock with any of the catalyst components described herein, which include a phosphorus stabilized zeolite with MSE zeolite structure (e.g., phosphorus stabilized MCM-68) and a non-zeolitic matrix. In certain embodiments, the contacting occurs with catalyst component being part of any of the catalyst compositions described herein.

In certain embodiments, a first butylenes to propylene selectivity ratio, attained from contacting the feedstock with any of the catalyst components described herein, which include a phosphorus stabilized zeolite with MSE zeolite structure (e.g., phosphorus stabilized MCM-68) and a non-zeolitic matrix, is greater than a second butylenes to propylene selectivity ratio, attained from contacting the feedstock with a catalyst component comprising a beta zeolite and/or a ZSM-5 zeolite without phosphorus stabilized zeolite with MSE zeolite structure (e.g., without phosphorus stabilized MCM-68).

In certain embodiments, the zeolite structure and activity may be evidenced by one or more of the following properties: zeolite surface area (ZSA), total surface area (TSA), steamed zeolite surface area (sZSA), total acidity, pore volume, TC4=(Total butylenes) yield, butylenes to propylene selectivity ratio, and the like. These values should be viewed as target achievable values and not inherent to the catalyst components or catalyst compositions described herein.

BRIEF DESCRIPTION OF THE DRAWINGS

The above and other features of the present disclosure, their nature, and various advantages will become more apparent upon consideration of the following detailed description, taken in conjunction with the accompanying drawings, in which.

DEFINITIONS

Figure 1A:
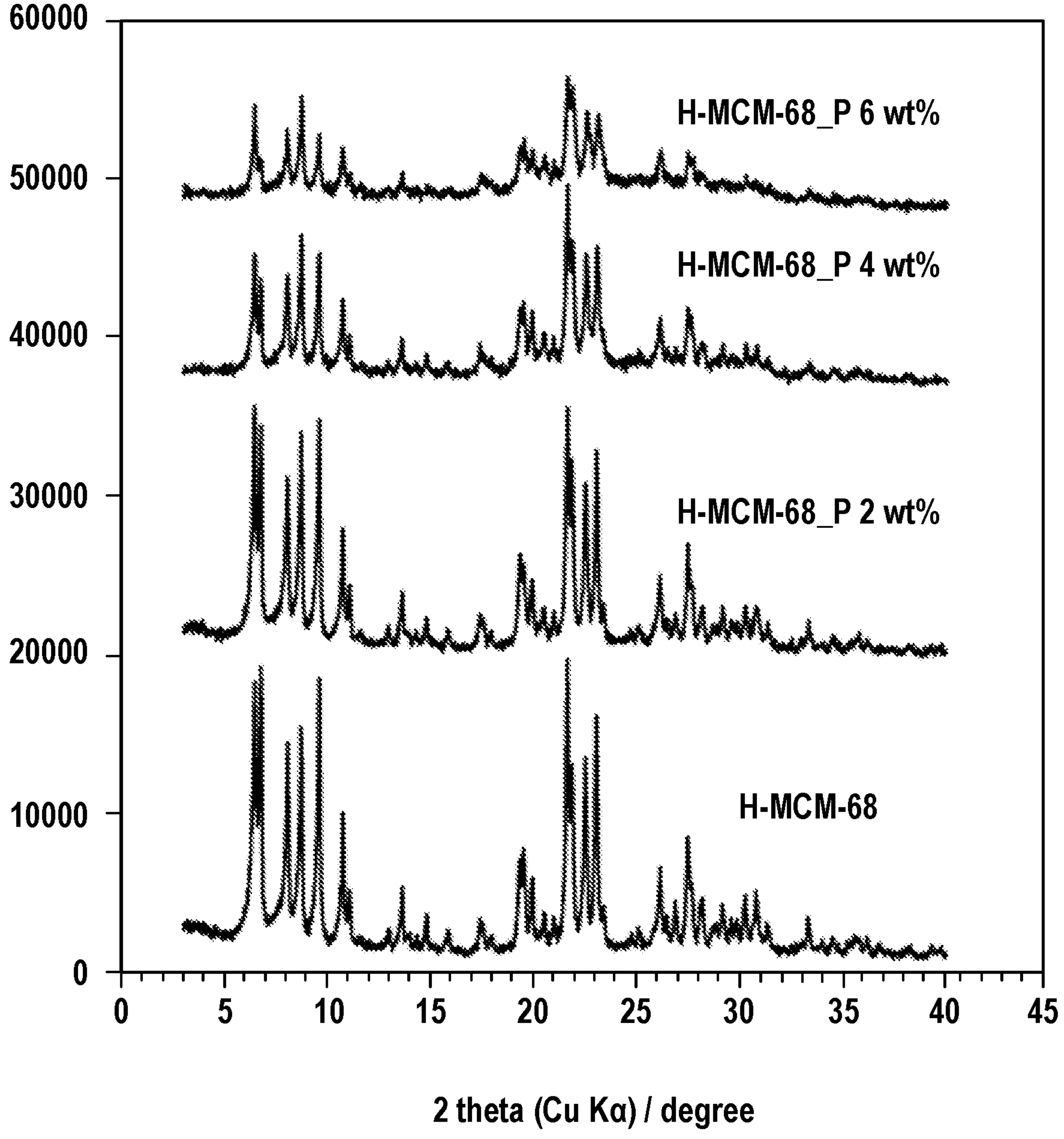
FIG. 1A illustrates the X-Ray Diffraction (XRD) pattern of catalyst components including MCM-68 zeolite.

As used herein, the singular forms "a," "an," and "the" include plural references unless the context clearly indicates otherwise. Thus, for example, reference to "a component" includes a single component as well as a mixture of two or more similar or different components, and the like.

As used herein, the term "about" in connection with a measured quantity, refers to the normal variations in that measured quantity, as expected by one of ordinary skill in the art in making the measurement and exercising a level of care commensurate with the objective of measurement and the precision of the measuring equipment. In certain embodiments, the term "about" includes the recited number ±10%, such that "about 10" would include from 9 to 11.

As used herein, the term "catalyst" or "catalyst composition" or "catalyst material" refers to a material that promotes a reaction. As used herein, the term "composition," when referring to a catalyst composition or an additive composition, refers to a blend or a mixture of two or more separate and distinct components, such as a first component mixed or blended with a second component. In certain embodiments, the components in the composition are chemically combined and cannot be separated through physical means (e.g., filtration). In other embodiments, the components in the composition are not chemically combined and may be separated through physical means (e.g., filtration).

As used herein, the term "fluid catalytic cracking" or "FCC" refers to a conversion process in petroleum refineries wherein high-boiling, high-molecular weight hydrocarbon fractions of petroleum crude oils are converted to more valuable gasoline, olefinic gases, and other products.

"Cracking conditions" or "FCC conditions" refers to typical FCC process conditions. Typical FCC processes are conducted at reaction temperatures of 4500 to 650° C. with catalyst regeneration temperatures of 600° to 850° C. Hot regenerated catalyst is added to a hydrocarbon feed at the base of a rise reactor. The fluidization of the solid catalyst particles may be promoted with a lift gas. The catalyst vaporizes and superheats the feed to the desired cracking temperature. During the upward passage of the catalyst and feed, the feed is cracked, and coke deposits on the catalyst.

The coked catalyst and the cracked products exit the riser and enter a solid-gas separation system, e.g., a series of cyclones, at the top of the reactor vessel. The cracked products are fractionated into a series of products, including gas, gasoline, light gas oil, and heavy cycle gas oil. Some heavier hydrocarbons may be recycled to the reactor.

As used herein, the term "feed" or "feedstock" refers to that portion of crude oil that has a high boiling point and a high molecular weight. In FCC processes, a hydrocarbon feedstock is injected into the riser section of an FCC unit, where the feedstock is cracked into lighter, more valuable products upon contacting hot catalyst circulated to the riser-reactor from a catalyst regenerator.

As used herein, "particles" can be in the form of microspheres which can be obtained by spray drying. As is understood by skilled artisans, microspheres are not necessarily perfectly spherical in shape.

As used herein, the terms "non-zeolitic component" or "matrix" or "non-zeolitic matrix" refer to the components of an FCC catalyst that are not zeolites or molecular sieves. As used herein, the non-zeolitic component can comprise binder and filler.

As used herein, the term "zeolite" refers to is a crystalline aluminosilicate with a framework based on an extensive three-dimensional network of silicon, aluminum and oxygen ions and have a substantially uniform pore distribution.

Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to illuminate certain materials and methods and does not pose a limitation on scope. No language in the specification should be construed as indicating any non-claimed element as essential to the practice of the disclosed materials and methods.

DETAILED DESCRIPTION

This disclosure is directed in certain embodiments to a catalyst component that includes a phosphorus stabilized zeolite having MSE zeolite structure, such as a phosphorus stabilized MCM-68, methods of preparation thereof, and methods of use thereof. In certain embodiments, this disclosure is directed to a catalyst composition that includes said catalyst component, methods of preparation thereof, and methods of use thereof.

The above-referenced catalyst component, referred to herein as first catalyst component and its methods of preparation will be described, followed by a description of catalyst compositions and their methods of preparation, and further followed be a description of the methods of using any of the first catalyst components and/or any of the catalyst compositions contemplated by this disclosure.

First Catalyst Component

In certain embodiments, the first catalyst component includes a zeolite having a MSE zeolite structure, such as MCM-68, that has been phosphorus stabilized, and a first non zeolitic matrix. The MSE zeolite structure refers to a porous crystalline material which contains at least one channel system, in which each channel is defined by a 12-membered ring of tetrahedrally coordinated atoms and at least two further, independent channel systems, in each of which each channel is defined by a 10-membered ring of tetrahedrally coordinated atoms, wherein the number of unique 10-membered ring channels being twice the number of 12-membered ring channels.

In certain embodiments, the dimensions of the 12 membered ring channel of the MSE zeolite structure is about 0.64×0.68 nm, the dimensions of one of the 10 membered ring channels of the MSE zeolite structure is about 0.52×0.58 nm, and the dimensions of the another of the 10 membered ring channels of the MSE zeolite structure is about 0.52×0.52 nm. An exemplary X-Ray Diffraction (XRD) pattern of a MSE zeolite structure is depicted in FIG. 1 (see MCM-68 curve).

In certain embodiments, the phosphorus stabilized MSE structure zeolite (e.g., phosphorus stabilized MCM-68) has a first XRD pattern that is substantially similar, in terms of peak locations and intensities, to a second XRD pattern of the same zeolite without phosphorus stabilization.

In certain embodiments, the silicon to aluminum ratio (SAR) of the phosphorus stabilized MSE structure zeolite (e.g., phosphorus stabilized MCM-68) ranges from any of about 5, about 6, about 7, about 8, about 9, about 10, about 11, about 12, about 13, or about 14 to any of about 15, about 20, about 25, about 30, about 35, about 40, about 45, about 50, about 55, or about 60, or any sub-range or single SAR value therein. In one embodiment, the SAR of the phosphorus stabilized MSE structure zeolite (e.g., phosphorus stabilized MCM-68) in the first catalyst component ranges from about 5 to about 60. In one embodiment, the SAR of the phosphorus stabilized MSE structure zeolite (e.g., phosphorus stabilized MCM-68) in the first catalyst component ranges from about 7 to about 30. In one embodiment, the SAR of the phosphorus stabilized MSE structure zeolite (e.g., phosphorus stabilized MCM-68) in the first catalyst component ranges from about 9 to about 15. Without being construed as limiting, it is believed that the SAR can be an important parameter which affects zeolite stability and activity. The SAR value should balance between maintaining the stability of the zeolite structure and the butylenes activity thereof.

The phosphorus content in the first catalyst component may range from any of about 0.5 wt. %, about 1 wt. %, about 1.5 wt. %, about 2 wt. %, about 2.5 wt. %, about 3 wt. %, or about 3.5 wt. % to any of about 4 wt. %, about 5 wt. %, about 6 wt. %, about 7 wt. %, about 8 wt. %, about 9 wt. %, or about 10 wt. %, or any sub-range or single phosphorus concentration value therein, based on the total weight of the zeolite in the first catalyst component. In one embodiment, the phosphorus content ranges from about 0.5 wt. % to about 10 wt. %, based on the total weight of the zeolite in the first catalyst component. In one embodiment, the phosphorus content ranges from about 1 wt. % to about 5 wt. %, based on the total weight of the zeolite in the first catalyst component. In one embodiment, the phosphorus content ranges from about 2 wt. % to about 4 wt. %, based on the total weight of the zeolite in the first catalyst component.

The first catalyst component may include the phosphorus stabilized MSE structure zeolite (e.g., phosphorus stabilized MCM-68) in an amount ranging from any of about 1 wt. %, about 2 wt. %, about 3 wt. %, about 4 wt. %, about 5 wt. %, about 6 wt. %, about 7 wt. %, about 8 wt. %, about 9 wt. %, about 10 wt. %, about 15 wt. %, about 20 wt. %, about 25 wt. %, about 30 wt. %, or about 35 wt. % to any of about 40 wt. %, about 45 wt. %, about 50 wt. %, about 55 wt. %, about 60 wt. %, about 65 wt. %, about 70 wt. %, about 75 wt. %, about 80 wt. %, about 85 wt. %, or about 90 wt. %, or any sub-range or single concentration value therein, based on total weight of the first catalyst component. The remainder may be a first non-zeolitic matrix and/or one or more additional zeolites.

The first non-zeolitic matrix may include one or more of clay, spinel, mullite, boehmite, alumina, silica, titania, zirconia, magnesia, kaolin, metakaolin, halloysite, kaolinite, dickite, nacrite, anauxite, silica-alumina, silica-magnesia, silica-zirconia, silica-thoria, silica-beryllia, silica-titania, silica-alumina-thoria, silica-alumina-zirconia, silica-alumina-magnesia, silica-magnesia-zirconia, rare earth-doped alumina (e.g., selected from one or more of ytterbium-doped alumina, gadolinium-doped alumina, cerium-doped alumina, or lanthanum-doped alumina), silica-doped alumina, gamma-alumina, α-alumina, χ-alumina, δ-alumina, θ-alumina, κ-alumina, or a mixture thereof.

The one or more additional zeolites may include zeolites with the structure BEA (e.g., beta zeolite), MSE, -SVR, FAU (e.g., zeolite Y), MOR, CON, SOF, MFI (e.g., ZSM-5), IMF, FER, MWW, MTT, TON, EUO, MRE, NAT, CHA, TUN, YFI, or a combination thereof. In certain embodiments, the one or more additional zeolites may include, without limitations, (1) large pore zeolites (e.g., those having pore openings greater than about 7 Angstroms) such as, for example, USY, REY, silicoaluminophosphates SAPO-5, SAPO-37, SAPO-40, MCM-9, metalloaluminophosphate MAPO-36, aluminophosphate VPI-5, or mesoporous crystalline material MCM-41; REUSY, zeolite X, zeolite Y, de-aluminated zeolite Y, silica-enriched de-aluminated zeolite Y, zeolite Beta, ZSM-3, ZSM-4, ZSM-18 and ZSM-20, (2) medium pore zeolites (e.g., those having pore openings of from about 4 Angstroms to about 7 Angstroms) such as, for example, ZSM-5, MCM-68, ZSM-11, ZSM-11 intermediates, ZSM-12, ZSM-22, ZSM-23, ZSM-35, ZSM-38, ZSM-48, ZSM-57 silicoaluminophosphate SAPO-31 and (3) small pore zeolites (e.g., those having pore openings of less than about 4 Angstroms) such as, for example, erionite and ZSM-34. In certain embodiments, the one or more additional zeolites may include, without limitations, zeolite A, zeolite B, zeolite F, zeolite H, zeolite K-G, zeolite L, zeolite M, zeolite Q, zeolite R, zeolite T, mordenite, erionite, offretite, ferrierite, chabazite, clinoptilolite, gmelinite, phillipsite and faujasite.

In certain embodiments, the BET total surface area (TSA) of the first catalyst component, prior to steaming and/or after steaming, ranges from any of about 150 $m^2/g$, about 175 $m^2/g$, about 200 $m^2/g$, about 225 $m^2/g$, about 250 $m^2/g$, about 275 $m^2/g$, about 300 $m^2/g$, about 325 $m^2/g$, about 350 $m^2/g$, about 375 $m^2/g$, or about 400 $m^2/g$ to any of about 425 $m^2/g$, about 450 $m^2/g$, about 475 $m^2/g$, about 500 $m^2/g$, about 525 $m^2/g$, about 550 $m^2/g$, about 575 $m^2/g$, about 600 $m^2/g$, about 625 $m^2/g$, about 650 $m^2/g$, about 675 $m^2/g$, about 700 $m^2/g$, about 725 $m^2/g$, or about 750 $m^2/g$, or any sub-range or single surface area value therein. In one embodiment, the BET total surface area of the first catalyst component, prior to steaming and/or after steaming, ranges from about 150 $m^2/g$ to about 750 $m^2/g$. In one embodiment, the BET total surface area of the first catalyst component, prior to steaming and/or after steaming, ranges from about 175 $m^2/g$ to about 675 $m^2/g$. In one embodiment, the BET total surface area of the first catalyst component, prior to steaming and/or after steaming, ranges from about 200 $m^2/g$ to about 600 $m^2/g$. Without being construed as limiting, it is believed that the butylenes activity (quantified as amount of butylenes per dose of the first catalyst component that is generated upon contacting at least the first catalyst component with a hydrocarbon feed), increases with increased zeolite surface area (ZSA) (or increased TSA) and/or with increased steamed zeolite surface area (SZSA) (or steamed TSA).

In certain embodiments, the first catalyst component has t-plot micropore volume, before steaming and/or after steaming, ranging from any of about 0.05 cc/g, about 0.06 cc/g, about 0.07 cc/g, about 0.08 cc/g, about 0.09 cc/g, about 0.10 cc/g, about 0.11 cc/g, about 0.12 cc/g, about 0.13 cc/g, about 0.14 cc/g, or about 0.15 cc/g to any of about 0.16 cc/g, about 0.17 cc/g, about 0.18 cc/g, about 0.19 cc/g, about 0.20 cc/g, about 0.21 cc/g, about 0.22 cc/g, about 0.23 cc/g, about 0.24 cc/g, about 0.25 cc/g, about 0.26 cc/g, about 0.27 cc/g, about 0.28 cc/g, about 0.29 cc/g, or about 0.30 cc/g, or any sub-range or single micropore volume value therein. In one embodiment, the first catalyst component has a t-plot micropore volume, before steaming and/or after steaming, ranging from about 0.05 cc/g to about 0.30 cc/g. In one embodiment, the first catalyst component has a t-plot micropore volume, before steaming and/or after steaming, ranging from about 0.06 cc/g to about 0.23 cc/g. In one embodiment, the first catalyst component has a t-plot micropore volume, before steaming and/or after steaming, ranging from about 0.07 cc/g to about 0.16 cc/g. Without being construed as limiting, it is believed that the micropore volume of the first catalyst component may be an important contributor to the butylenes related activity of the first catalyst component.

In certain embodiments, the first catalyst component has a total acidity, before steaming and/or after steaming, ranging from about 0.3 mmol/(g catalyst) to about 0.7 mmol/(g catalyst), from about 0.3 mmol/(g catalyst) to about 0.6 mmol/(g catalyst), or from about 0.3 mmol/(g catalyst) to about 0.5 mmol/(g catalyst), or any sub-range or single total acidity value therein. Without being construed as limiting, it is believed that the total acidity of the first catalyst component may be a reflection of the butylenes related activity of the first catalyst component. The total acidity, which provides information about the total number of acid sites in the tested catalyst component, is measured by $NH_3$ temperature programmed desorption.

Preparation of the first catalyst component, in accordance with one embodiment of this disclosure, begins by combining a silicon source (e.g., colloidal $SiO_2$), an aluminum source (e.g., $Al(OH)_3$), a base (e.g., KOH), and water and stirring the mixture for a first duration. The initial stirring may be performed at room temperature for about 10 minutes to about 60 minutes, about 15 minutes to about 45 minutes, or about 20 minutes to about 40 minutes. The amount of silicon source and aluminum source added may be adjusted to attain a target SAR. The type of silicon source, aluminum source, or base should not be construed as limiting. Other suitable silicon sources, aluminum sources, or bases, may be used, as can be readily identified by those skilled in the art.

Thereafter, a structure directing agent (SDA), such as SDA with the below chemical structure, may be added to the mixture, followed by stirring the SDA and the mixture for a second duration.

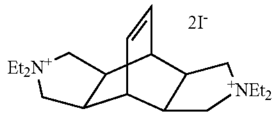

The stirring of the SDA and the mixture may be performed at room temperature for about 1 hours to about 10 hours, about 2 hours to about 7 hours, or about 3 hours to about 5 hours.

Thereafter, the stirred mixture with SDA may undergo hydrothermal synthesis at an elevated temperature for a third duration. The hydrothermal synthesis may occur at a temperature ranging from about 100° C. to about 250° C., from about 120° C. to about 200° C., or from about 140° C. to about 180° C. The third duration of the hydrothermal synthesis may range from about 1 day to about 30 days, from about 5 days to about 25 days, or from about 10 days to about 20 days.

In certain embodiments, once hydrothermal synthesis of the MSE structured zeolite (e.g., MCM-68) and the crystallization process has been completed, the slurry may be filtered to separate the MSE structured zeolite from a substantial portion of its mother liquor. The microspheres may be washed, e.g., by contacting them with water either during or after filtration. The purpose of the washing step is to remove mother liquor that would otherwise be left entrained within the microspheres. Subsequently, the microspheres may be dried. Drying may occur at a temperature ranging from about 40° C. to about 120° C., from about 60° C. to about 100° C., or from about 70° C. to about 90° C. The drying duration may range from about 2 hours to about 72 hours, from about 5 hours to about 24 hours, or from about 8 hours to about 15 hours.

The process for preparing the first catalyst component may further include modifying or stabilizing the synthesized MSE structured zeolite (e.g., synthesized MCM-68) with phosphorus. Modifying or stabilizing may, in certain embodiments, include impregnating the synthesized MSE structured zeolite (e.g., synthesized MCM-68) with phosphorus. The impregnation may be through incipient wetness impregnation with a phosphorus source. Suitable phosphorus sources may include, without limitations, phosphoric acid, di-ammonium phosphate, or a combination thereof. In certain embodiments, other methods for modifying or stabilizing the MSE structured zeolite (e.g., MCM-68) with phosphorus may be utilized. The amount of phosphorus source utilized may be adjusted to achieve a target phosphorus content in the first catalyst component.

The phosphorus stabilized MSE structured zeolite (e.g., phosphorus stabilized MCM-68) may be dried (in addition to the previous drying step or instead of the previous drying step described prior to the phosphorus modification/stabilization). In certain embodiments, drying of the phosphorus stabilized MSE zeolite may occur at a temperature ranging from about 40° C. to about 250° C., from about 80° C. to about 200° C., or from about 100° C. to about 140° C. The drying duration of the phosphorus stabilized MSE zeolite may range from about 2 hours to about 72 hours, from about 5 hours to about 24 hours, or from about 8 hours to about 15 hours.

The process for preparing the first catalyst component may further include calcining the phosphorus stabilized MSE structured zeolite (e.g., phosphorus stabilized MCM-68), e.g., in a muffle furnace. The calcination duration may range from about 30 minutes to about 10 hours, from about 1 hours to about 8 hours, or from about 2 hours to about 4 hours. The calcination temperature may range from about 400° C. to about 800° C., from about 500° C. to about 750° C., or from about 600° C. to about 700° C. The calcination temperature and duration should not be construed as limiting. Under various circumstances, other calcination durations and temperatures may be utilized.

The process described here for preparing the first catalyst component should not be construed as limiting. In certain embodiments, one or more drying steps may be implemented at various parts of the process, one or more calcination steps may be implemented at various parts of the process, one or more phosphorus stabilization/modification steps may be implemented at various parts of the process, and the like. Similarly, the order of steps should not be construed as limiting and it should be understood that phosphorus stabilization/modification and/or drying and/or calcination (and optionally other steps) may be introduced at a different step in the process than described hereinabove. It should also be understood that in certain embodiments, a single entity will conduct all of the above process steps, while in alternative embodiments, two or more entities will perform the above process steps.

It is believed, without being construed as limiting, that inclusion of phosphorus in the first catalyst component stabilized the first catalyst component against steam treatment, which is believed to contribute to improved performance in fluid catalytic cracking and/or hydrocracking applications. Different zeolite structures behave differently under severe conditions, such as steam treatment, and hence, each zeolite would benefit from a customized stabilization techniques, if needed. For certain zeolite structures, such zeolite Y, rare earth cations may be used for structure stabilization. A stabilization technique that may work for one zeolite structure may not necessarily work for a different zeolite structure. Notwithstanding the above, it was surprisingly identified herein, that phosphorus may be used for structure stabilization of an MSE structured zeolite such as MCM-68 under steam treatment conditions.

Catalyst Composition

In certain embodiments, the instant disclosure is directed to a catalyst composition that includes any of the first catalyst components described herein along with a second catalyst component and optionally with at least one additional component. The second catalyst composition being compositionally different from the first catalyst component. Any additional component that may be present may also be compositionally different from the first catalyst component and from the second catalyst component.

The second catalyst component may include a second zeolite and a second non-zeolitic matrix. Each at least one additional component may include a respective one additional non-zeolitic matrix. In certain embodiments, the at least one additional component includes at least one additional zeolite.

The second zeolite and/or the at least one additional zeolite may be independently selected from zeolites with the structure BEA (e.g., beta zeolite), MSE, -SVR, FAU (e.g., zeolite Y), MOR, CON, SOF, MFI (e.g., ZSM-5), IMF, FER, MWW, MTT, TON, EUO, MRE, NAT, CHA, TUN, YFI, or a combination thereof. In certain embodiments, the second zeolite and/or at least one additional zeolites may be independently selected from, without limitations, (1) large pore zeolites (e.g., those having pore openings greater than about 7 Angstroms) such as, for example, USY, REY, silicoaluminophosphates SAPO-5, SAPO-37, SAPO-40, MCM-9, metalloaluminophosphate MAPO-36, aluminophosphate VPI-5, or mesoporous crystalline material MCM-41; REUSY, zeolite X, zeolite Y, de-aluminated zeolite Y, silica-enriched de-aluminated zeolite Y, zeolite Beta, ZSM-3, ZSM-4, ZSM-18 and ZSM-20, (2) medium pore zeolites (e.g., those having pore openings of from about 4 Angstroms to about 7 Angstroms) such as, for example, ZSM-5, MCM-68, ZSM-11, ZSM-11 intermediates, ZSM-12, ZSM-22, ZSM-23, ZSM-35, ZSM-38, ZSM-48, ZSM-57 silicoaluminophosphate SAPO-31 and (3) small pore zeolites (e.g., those having pore openings of less than about 4 Angstroms) such as, for example, erionite and ZSM-34. In certain embodiments, the second zeolite and/or the at least one additional zeolites may be independently selected from, without limitations, zeolite A, zeolite B, zeolite F, zeolite H, zeolite K-G, zeolite L, zeolite M, zeolite Q, zeolite R, zeolite T, mordenite, erionite, offretite, ferrierite, chabazite, clinoptilolite, gmelinite, phillipsite, faujasite, and a combination thereof.

Hydrothermally and/or chemically modified versions of many of the zeolites described above may also be suitably used in the second catalyst component and/or in the at least one additional component (if present) in the catalyst compositions contemplated herein.

In one embodiment, the second zeolite in the second component and/or the at least one additional zeolite in the at least one additional component (if present) includes large pore molecular sieve zeolite having a pore size greater than 7 angstroms. In one embodiment, the second zeolite in the second component and/or the at least one additional zeolite in the at least one additional component (if present) includes zeolite Y. In one embodiment, the second zeolite in the second component and/or the at least one additional zeolite in the at least one additional component (if present) includes ZSM-5, beta zeolite, or a combination thereof. In one embodiment, the second zeolite in the second component is Y zeolite, and the at least one additional zeolite in the at least one additional component (if present) is ZSM-5, beta zeolite, or a combination thereof. In one embodiment, the second zeolite in the second component is a combination of Y zeolite with at least one of ZSM-5 and beta zeolite.

The second non-zeolitic matrix and/or at least one additional non-zeolitic matrix in the at least one additional component (if present) may independently include one or more of clay, spinel, mullite, boehmite, alumina, silica, titania, zirconia, magnesia, kaolin, metakaolin, halloysite, kaolinite, dickite, nacrite, anauxite, silica-alumina, silica-magnesia, silica-zirconia, silica-thoria, silica-beryllia, silica-titania, silica-alumina-thoria, silica-alumina-zirconia, silica-alumina-magnesia, silica-magnesia-zirconia, rare earth-doped alumina (e.g., selected from one or more of ytterbium-doped alumina, gadolinium-doped alumina, cerium-doped alumina, or lanthanum-doped alumina), silica-doped alumina, gamma-alumina, $\alpha$-alumina, $\chi$-alumina, $\delta$-alumina, $\theta$-alumina, $\kappa$-alumina, or a mixture thereof.

Any of the first catalyst components described herein may be present in any of the catalyst compositions contemplated herein in an amount ranging from any of about 1 wt. %, about 1.5 wt. %, about 2.0 wt. %, about 2.5 wt. %, about 3.0 wt. %, about 3.5 wt. %, about 4.0 wt. %, about 4.5 wt. %, about 5.0 wt. %, about 5.5 wt. %, about 6.0 wt. %, about 6.5 wt. %, about 7.0 wt. %, about 7.5 wt. %, about 8.0 wt. %, about 8.5 wt. %, about 9.0 wt. %, or about 9.5 wt. % to any of about 10 wt. %, about 11 wt. %, about 12 wt. %, about 13 wt. %, about 14 wt. %, about 15 wt. %, about 16 wt. %, about 17 wt. %, about 18 wt. %, about 19 wt. %, about 20 wt. %, about 21 wt. %, about 22 wt. %, about 23 wt. %, about 24 wt. %, or about 25 wt. %, or any sub-range or single concentration value therein, based on total weight of the catalyst composition. In one embodiment, the first catalyst composition is present in the catalyst composition in an amount ranging from about 1 wt. % to about 25 wt. %, based on the total weight of the catalyst composition. In one embodiment, the first catalyst composition is present in the catalyst composition in an amount ranging from about 1.5 wt. % to about 15 wt. %, based on the total weight of the catalyst composition. In one embodiment, the first catalyst composition is present in the catalyst composition in an amount ranging from about 2 wt. % to about 10 wt. %, based on the total weight of the catalyst composition.

The second catalyst component and/or any additional component, cumulatively, are present in the catalyst composition in an amount that, together with the concentration of the first catalyst component, will add up to a 100 wt. %.

In certain embodiments, the second catalyst component includes a large pore molecular sieve zeolite having a pore size greater than 7 angstrom (such as, without limitations, zeolite Y, dealuminated zeolite Y, silica-enriched dealuminated zeolite Y, REY, USY, CREY, REUSY, and the like) that is present in the catalyst composition in an amount ranging from any of about 40 wt %, about 45 wt %, about 50 wt %, about 55 wt %, about 60 wt %, about 65 wt %, about 70 wt %, about 75 wt %, or about 80 wt % to any of about 85 wt %, about 90 wt %, about 91 wt %, about 92 wt %, about 93 wt %, about 94 wt %, about 95 wt %, or about 96 wt %, or any sub-range or single value therein, based on total weight of the catalyst composition.

In certain embodiments, the at least one additional component is present in the catalyst composition in an amount ranging from any of about 0.5 wt %, about 1 wt %, about 1.5 wt %, about 2 wt %, about 2.5 wt %, or about 3 wt % to any of about 4 wt %, about 5 wt %, about 6 wt %, about 7 wt %, about 8 wt %, about 9 wt %, about 10 wt %, or about 15 wt %, or any sub-range or single value therein, based on total weight of the catalyst composition.

In certain embodiments, the amount of the first catalyst component in the catalyst composition is lower than the amount of the second catalyst component. For instance, the wt:wt ratio of the first catalyst component to the second catalyst component in the FCC catalyst composition may range from about 1:1.5 to about 1:20, from about 1:3 to about 1:15, or from about 1:5 to about 1:13, or any sub-range or single ratio value therein.

In certain embodiments, the instant disclosure is directed to a method for preparing any of the catalyst compositions described herein by combining any of the first catalyst components described herein with a second catalyst component and optionally with at least one additional component, if present. The process may further include preparing each of the components in the catalyst composition, such as, preparing the first catalyst component and/or preparing the second catalyst component and/or preparing any additional component that may be present in the composition.

In certain embodiments, the various components may be formulated as separate and distinct particles. In this manner, the first catalyst component may be add to the FCC catalyst composition as needed to provide a customized catalyst solution with customized performance. The catalyst composition may be designed to exhibit enhanced performance, such as improved total butylenes yield, improved butylenes to propylene selectivity ratio, enhanced catalytic stability (e.g., stability of the zeolite structures in the catalyst components and/or catalyst composition), and the like.

Methods of Use

While MSE structured zeolites have been used in certain reactions, such as methanol to olefin (MTO), methanol to propylene (MTP), isomerization, alkylation, dimethoxyethane to light olefins, and the like, these zeolites have been of lesser interest in the fluid catalytic cracking (FCC) realm. The reaction pathways for the reactions described above and the reactions contemplated herein are different. Furthermore, issues that arise from steam deactivation of the catalyst component and the need for zeolite structure stabilization are not evident with the reactions described above.

Hence, in certain embodiments, the instant disclosure is directed to the use of any of the first catalyst components described herein and/or to the use of any of the catalyst compositions described herein in petroleum refining applications, such as fluid catalytic cracking and/or hydrocracking.

Fluid catalytic cracking (FCC) is one type of catalytic cracking process that is widely used. The process typically employs a powdered catalyst having the particles suspended in a rising flow of feed hydrocarbons to form a fluidized bed. Zeolite-based catalysts are commonly used as are composite catalysts which contain zeolites, silica-aluminas, alumina and other binders. In representative processes, cracking takes place in a riser, which is a vertical or upward sloped pipe.

A pre-heated feed (e.g., a vacuum gas oil) may be sprayed into the base of the riser via feed nozzles where it contacts hot fluidized catalyst at a temperature between about 400° C. and about 800° C. The feed is vaporized on contact with the catalyst and the cracking occurs converting the high molecular weight oil into lighter components including liquefied petroleum gas (LPG), gasoline, and a distillate. The catalyst-feed mixture flows upward through the riser for a short period (few seconds) and then the mixture is separated in cyclones. The hydrocarbons thus separated from the catalyst are directed to a fractionator for separation into LPG, gasoline, diesel, kerosene, jet fuel, and other possible fractions.

While going through the riser, the cracking catalyst is deactivated because the process is accompanied by formation of deposit coke on the catalyst particles. So contaminated catalyst is separated from the cracked hydrocarbon vapors and is further treated with steam to remove hydrocarbons remaining in the catalyst's pores. The catalyst is then directed into a regenerator where the coke is burned off the catalyst particles surface, thus restoring the catalyst's activity and providing the necessary heat for the next reaction cycle. The process of cracking is endothermic. The regenerated catalyst is then used in the new cycle. New catalysts for catalytic cracking processes such as FCC should therefore be capable of regeneration. The MCM-68 zeolite and first catalyst component, in one embodiment, is stable with regard to regeneration.

Catalytic cracking processes may be carried out with the first catalyst component and/or catalyst composition described herein using feedstocks such as gas oils, heavy naphtha, cycle oils, deasphalted crude oil residua, Fischer-Tropsch wax, slack wax, hydrotreated products of the foregoing and combinations thereof, with gasoline being the typically desired product. Temperature conditions of from about 400° C. to about 800° C., pressure conditions of from about 0 to about 688 kPa g (about 0 to 100 psig) and contact times of from about 0.1 seconds to about 1 hour are suitable. Temperature conditions of from about 450° C. to about 700° C., pressure conditions of from about 0 to about 344 kPa·g (about 0 to 50 psig) and contact times of from about 0.1 seconds to about several minutes are often preferred. The preferred conditions are determined based on the hydrocarbon feedstock being cracked and the cracked products desired.

Naphtha cracking processes may be carried out with the first catalyst component and/or catalyst composition described herein using a naphtha feedstock, such as, but not limited to, straight-run naphtha, Coker naphtha, Visbreaker naphtha, FCC naphtha, and Catalytic Polymerization naphtha (Cat Poly naphtha) which are catalytically cracked to light olefins such as ethylene and propylene. The naphtha is contacted with the first catalyst component in, for example, a fluidized catalytic cracking (FCC) type reactor. The choice of reactor can be any type of reactor for intimately mixing the naphtha feedstream with the catalyst. Reactors of this type are well known to those skilled in the art.

Alternatively, reactor types such as moving bed reactors with continuous catalyst regeneration, or fixed bed reactors with periodic catalyst regeneration by pressure swing or temperature swing may be utilized to contact the hydrocarbon feed with the first catalyst component. New catalysts for catalytic cracking processes such as naphtha cracking should therefore be capable of regeneration. The MCM-68 zeolite and first catalyst component, in one embodiment, is stable with regard to regeneration.

The naphtha cracking reactions can be carried out between a temperature of about 400° C. to about 700° C. The cracking process may be carried out using pressure conditions of from about 0 to about 688 kPa·g (about 0 to 100 psig) and a contact time from about 0.1 seconds to about 1 hour and preferably from about 0.1 seconds to about 0.1 hour. The longer contact times are used at lower temperatures while shorter times are used at higher temperatures, assuming all other process variables are equal.

Olefin cracking processes are preferably carried out with the first catalyst component and/or catalyst composition using feedstocks such as a mixed olefin stream comprising $C_4$ or $C_5$ to $C_{10}$ olefins, with ethylene, propylene, and butylene being the principal desired products. The operation of an olefin cracking reactor is at a temperature from 400° C. to 650° C., and preferably between 500° C. to 600° C. The pressure for the olefin cracking reactor during operation is between 0 kPa to 344 kPa, with a preferred operating pressure between 10 kPa to 200 kPa for the olefin partial pressure. The contact time for the olefin cracking process is from about 0.1 seconds to about 1 hour.

The $C_4$ or $C_5$ to $C_{10}$ olefin feedstock is passed over a first catalyst component and/or catalyst composition to crack the olefins into smaller molecules. The cracking process generates some coking on the catalyst component and/or catalyst composition, and over time the catalyst activity is reduced due to plugging of the catalyst pores with coke. The catalyst component and/or catalyst composition may be regenerated though oxidizing the coke and removing it as gas comprising primarily $N_2$, $H_2O$, CO and $CO_2$. The catalyst in the reactors may be regenerated periodically, and therefore the process may swing between multiple reactors on a frequent basis. Alternatively, reactor types such as moving or fluidized bed reactors with continuous catalyst regeneration may be utilized to contact the hydrocarbon feed with the first catalyst component and/or catalyst composition. New catalysts for catalytic cracking processes such as olefin cracking should therefore be capable of regeneration. The first catalyst component and/or catalyst composition described herein, in one embodiment, are stable with regard to regeneration.

In certain embodiments, the instant disclosure encompasses a process for catalytic cracking and/or hydrocracking of a hydrocarbon feedstock by contacting the feedstock with any of the first catalyst components described herein or any of the catalyst compositions described herein. In one embodiment, the instant disclosure is directed to a process for catalytic cracking and/or hydrocracking of a hydrocarbon feedstock by contacting the feedstock with a first catalyst component that includes a phosphorus stabilized MSE structured zeolite (such as phosphorus stabilized MCM-68) and a first non-zeolitic matrix. The first catalytic component may have any of the characteristics described hereinbefore with respect to, without limitations, phosphorus content, porous crystalline structure, total acidity, SAR, micropore volume, surface area, or a combination thereof. In one embodiment, the instant disclosure is directed to a process for catalytic cracking and/or hydrocracking of a hydrocarbon feedstock by contacting the feedstock with any of the catalyst compositions described herein (which include any of the first catalyst components described herein, a second catalyst component, and optionally at least one additional component). The catalyst composition and its constituents may have any of the characteristics described hereinabove with respect to, without limitations, concentration of the various constituents, composition of the various constituents, or a combination thereof.

In certain embodiments, the first catalyst components described herein and/or the catalyst compositions described herein have higher selectivity towards butylenes and higher total butylenes yield compared to, e.g., ZSM-5, which is a commonly used zeolite for cracking towards small olefins.

In one embodiment, contacting a first catalyst component as described herein and/or a catalyst composition as described herein with a hydrocarbon feedstock under FCC conditions exhibits a first butylenes to propylene selectivity ratio, while contacting the same hydrocarbon feedstock under the same FCC conditions with a catalyst component comprising ZSM-5 and no phosphorus stabilized MCM-68 exhibits a second butylenes to propylene selectivity that is lower than the first butylenes to propylene selectivity ratio.

In certain embodiments, the methods of cracking a hydrocarbon feed, as described herein, result in an average butylenes to propylene selectivity ratio that is greater than about 0.7, greater than about 0.8, greater than about 0.85, greater than about 0.9, or greater than about 0.95, or greater than about 1. In one embodiment, the method of cracking a hydrocarbon feed, as described herein, results in an average butylene to propylene selectivity ratio that is greater than about 0.7. In one embodiment, the method of cracking a hydrocarbon feed, as described herein, results in an average butylenes to propylene selectivity ratio that is greater than about 0.8. In one embodiment, the method of cracking a hydrocarbon feed, as described herein, results in an average butylenes to propylene selectivity ratio that is greater than about 0.85. In one embodiment, the method of cracking a hydrocarbon feed, as described herein, results in an average butylenes to propylene selectivity ratio that is greater than about 0.9. In one embodiment, the method of cracking a hydrocarbon feed, as described herein, results in an average butylenes to propylene selectivity ratio that is greater than about 0.95. In one embodiment, the method of cracking a hydrocarbon feed, as described herein, results in an average butylenes to propylene selectivity ratio that is greater than about 1.

In one embodiment, contacting a first catalyst component as described herein and/or a catalyst composition as described herein with a hydrocarbon feedstock under FCC conditions exhibits a first total butylenes yield (at a given conversion value), while contacting the same hydrocarbon feedstock under the same FCC conditions with a catalyst component comprising ZSM-5 and no phosphorus stabilized MCM-68 exhibits a second total butylenes yield (at the same conversion value) that is substantially similar or lower than the first total butylenes yield.

In certain embodiments, the first catalyst components described herein and/or the catalyst compositions described herein exhibit enhanced performance with respect to favorable products, such as butylenes, while suppressing selectivity toward less favorable products, such as, benzene, toluene, xylene (BTX), methane, C6, and C7.

In certain embodiments, the instant disclosure is directed to a process for stabilizing the catalytic activity (after steaming) of a catalyst component including an MSE structured zeolite (such as MCM-68) by modifying the MSE structured zeolite (such as MCM-68) with a phosphorus containing compound. Preservation of the catalytic activity after steaming may be assessed by comparing before steaming and after steaming values for parameters such as, without limitations, total butylenes yield at a certain conversion value, the butylenes to propylene selectivity ratio, SAR, zeolite surface area, micropore volume, total acidity, or a combination thereof. In certain embodiments, any of the above parameters remain substantially similar for the first catalyst components described herein and/or for the catalyst compositions described herein before steaming and after steaming. Furthermore, in certain embodiments, any of the above parameters remain substantially similar for the first catalyst components described herein (whether before steaming or after steaming) as compared to the first catalyst component without phosphorus stabilization/modification and before steaming. Exemplary steaming conditions include steam treating at 816° C. for about 4 hours at a flow rate of 1 ml/min. In some embodiments, the steaming is conducted for about one to about 24 hours. The steaming temperature and duration should not be construed as limiting. Under various circumstances, other steaming durations and temperatures may be utilized.

The term "substantially similar," as used herein, refers to a particular value being within about 5%, within about 10%, or within about 15% of the value that it is being compared to.

ILLUSTRATIVE EXAMPLES

The following examples are set forth to assist in understanding the disclosure and should not be construed as specifically limiting the invention described and claimed herein. Such variations of the invention, including the substitution of all equivalents now known or later developed, which would be within the purview of those skilled in the art, and changes in formulation or minor changes in experimental design, are to be considered to fall within the scope of the invention incorporated herein.

Example 1: Hydrothermal Synthesis of MCM-68

A mixture of 100 mmol of $SiO_2$, 10 mmol $Al(OH)_3$, 3000 mmol water, and 37.5 mmol KOH were mixed for a duration of about 30 minutes at room temperature. About 10 mmol of a structure directing agent (SDA) having the below chemical structure was added to the mixture followed by stirring for about 4 hours at room temperature:

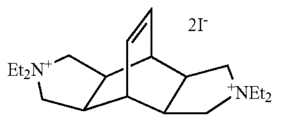

The mixture with the SDA underwent hydrothermal synthesis for about 16 days at a temperature of about 160° C., followed by filtration, washing, and drying at about 80° C. overnight to form "[Al]-MCM-68 as-made." The [Al]-

MCM-68 as-made was calcined for about 10 hours at 650° C. to form "[Al]-MCM-68(X)," where X represents the silica to alumina ratio (SAR) as can be estimated by Inductively Coupled Plasma Atomic Emission Spectroscopy (ICP-AES).

Example 2: Effect of Phosphorus Modification on MSE Structure of MCM-68

The X-Ray Diffraction pattern of the MCM-68 synthesized in example 1 was determined prior to steaming (see FIG. 1A) and after steaming (see FIG. 1).

FIG. 1A illustrates the X-Ray Diffraction (XRD) pattern of catalyst components including MCM-68 zeolite prior to steaming and without phosphorus modification ("H-MCM-68"), prior to steaming but after phosphorus modification with 2 wt. % phosphorus ("H-MCM-68_P 2 wt %"), prior to steaming but after phosphorus modification with 4 wt. % phosphorus ("H-MCM-68_P 4 wt %"), prior to steaming but after phosphorus modification with 6 wt. % phosphorus ("H-MCM-68_P 6 wt %").

Figure 1B:
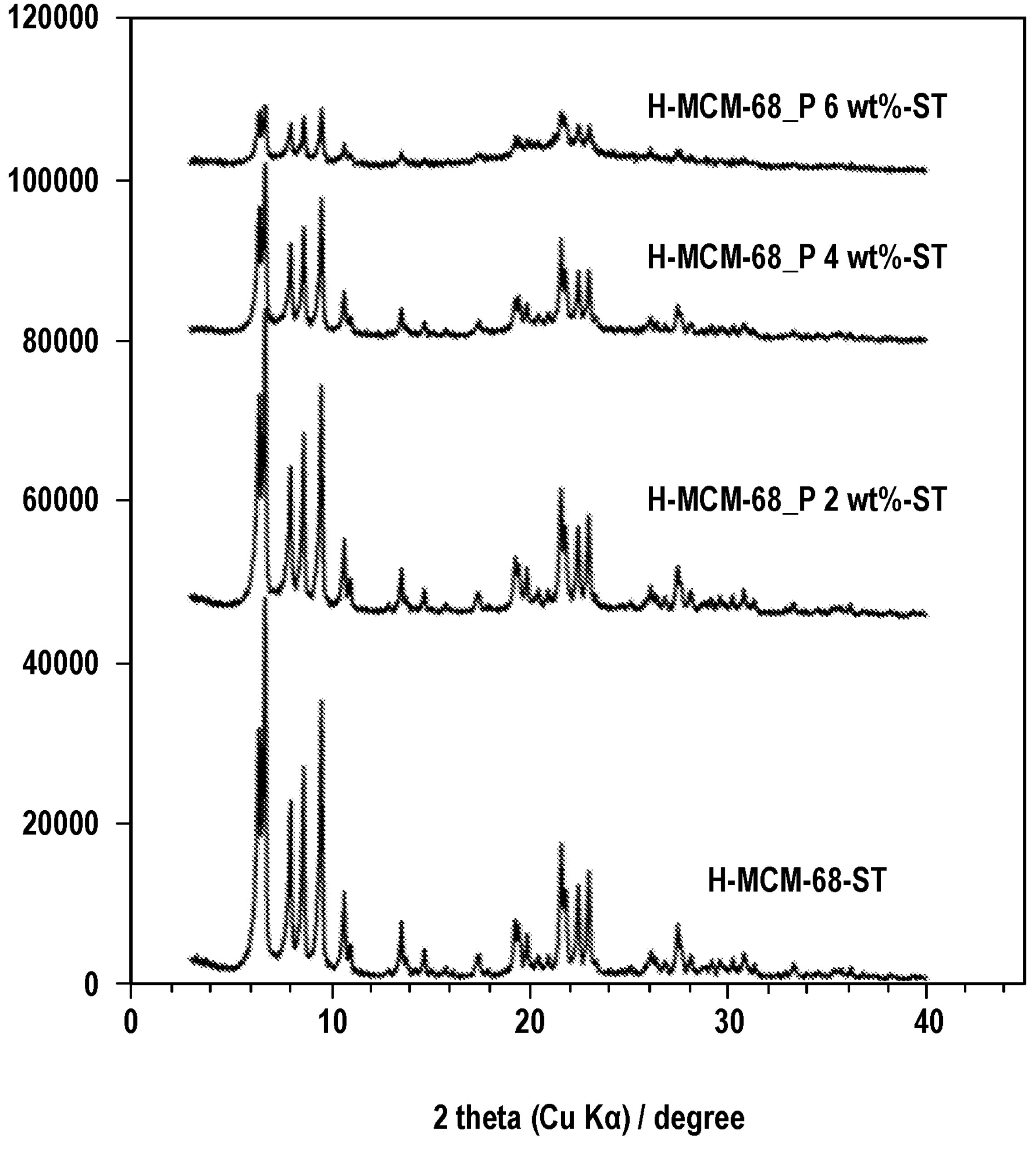
FIG. 1B illustrates the XRD pattern of the same catalyst components as in FIG. 1A, after steaming.

FIG. 1B illustrates the XRD pattern of the same catalyst components as in FIG. 1A, after steaming. Specifically, a catalyst component after steaming and without phosphorus modification ("H-MCM-68-ST"), a catalyst component after phosphorus modification with 2 wt. % phosphorus and steaming ("H-MCM-68_P 2 wt %-ST"), a catalyst component after phosphorus modification with 4 wt. % phosphorus and steaming ("H-MCM-68_P wt %-ST"), and a catalyst component after phosphorus modification with 6 wt. % phosphorus and steaming ("H-MCM-68_P 6 wt %-ST").

Phosphorus modification was attained by taking about 0.6 g of the MCM-68 zeolite containing catalyst component and performing incipient wetness impregnation with an appropriate amount of di-ammonium phosphate. The phosphorus impregnated catalyst component was dried at 120° C. for 12 hours followed by calcination at 650° C. for about 3 hours in a muffle furnace. The steaming conditions for the steamed phosphate modified catalyst component were a flow of water at a rate of 1 ml/min at 816° C. for 4 hours.

As can be seen from FIGS. 1A and 1B, the MSE structure of the MCM-68 is retained after phosphorus modification and/or after steaming.

Example 3: Performance of MCM-68 Zeolite (with and without P Modification) in 1-Octene Cracking Reaction The performance of MCM-68 zeolite containing catalyst component (with and without phosphorus modification), before and after steaming, was compared to that of a base catalyst, in a cracking reaction of 1 octene. The reaction conditions were: 2.5 mg of a catalyst component, $P_{1\text{-}octene}$ was 33 kPa, temperature was 600° C., and argon flow rate was 30 ml/min. The pre-treatment conditions were air flow rate of 21.4 ml/min at 600° C. for 1 hour. The steaming conditions were water flowing at a rate of 1 ml/min at 816° C. for 4 hours.

Five catalyst components were assessed: A) A catalyst component including MCM-68 zeolite (FIG. 2A, "MCM-68"), B) a catalyst component including MCM-68 after steaming at the above steaming conditions (FIG. 2B, "MCM-68_ST"), C) a catalyst component including MCM-68 modified with 2 wt. % phosphorus after steaming at the above steaming conditions (FIG. 2C, "2 wt % P/MCM-68_ST"), D) a catalyst component including MCM-68 modified with 4 wt. % phosphorus after steaming at the above steaming conditions (FIG. 2D, "4 wt % P/MCM-68_ST"), and E) a catalyst component including ZSM-5 as the base catalyst (B) after steaming at the above steaming conditions (FIG. 2E, "B_ST").

Figures 2A, 2B, 2C, 2D, 2E:
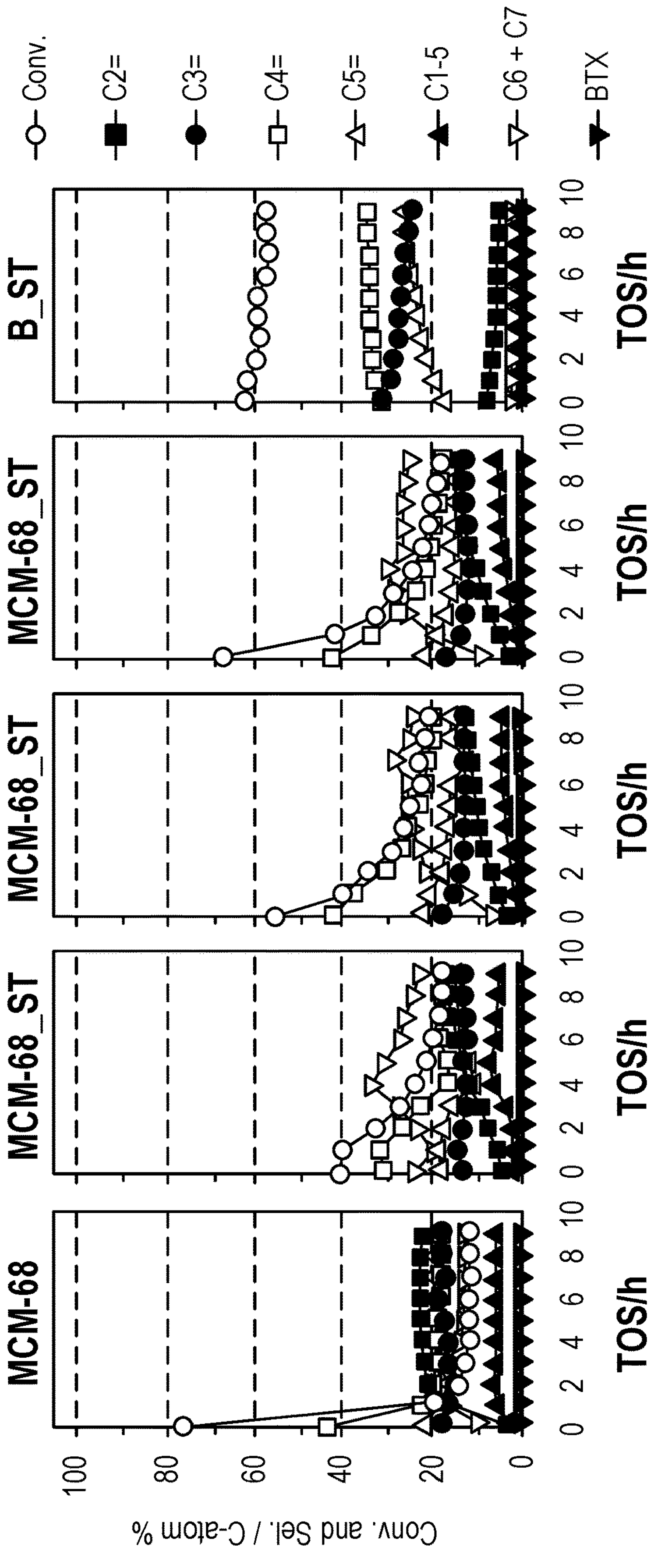
FIG. 2A depicts the performance (in terms of conversion and selectivity) of catalyst components including MCM-68 zeolite prior to steaming and without phosphorus modification.
FIG. 2B depicts the performance (in terms of conversion and selectivity) of catalyst components including MCM-68 zeolite after steaming and without phosphorus modification.
FIG. 2C depicts the performance (in terms of conversion and selectivity) of catalyst components including MCM-68 zeolite after phosphorus modification with 2 wt. % phosphorus and steaming.
FIG. 2D depicts the performance (in terms of conversion and selectivity) of catalyst components including MCM-68 zeolite after phosphorus modification with 4 wt. % phosphorus and steaming.
FIG. 2E depicts the performance (in terms of conversion and selectivity) of catalyst components including MCM-68 zeolite and for a comparative base catalyst component including ZSM-5 zeolite.

As can be seen in FIG. 2A, the conversion of 1-octene to butylenes is close to about 80% in a catalyst component including MCM-68 prior to P modification or steaming. This conversion is higher than that of the base catalyst, which is about 60% as seen in FIG. 2E. However, after steaming a catalyst component including MCM-68 without P modification, the conversion reduces to 40%, as seen in FIG. 2B. Surprisingly, phosphorus modification of the MCM-68 provides for a catalyst component that maintains a high conversion value, comparable to that of the base catalyst or higher, even after steaming, as seen in FIG. 2C (about 60% conversion) and 2D (about 70% conversion).

It is also evident from FIGS. 2A through 2D, that catalyst components that include MCM-68 zeolite (whether phosphorus modified or not) generate far more butylenes (C4=total) as compared to propylene (C3), particularly at earlier time points (e.g., up to about 4 hours). In contrast, during the initial four hours of the 1-octene cracking reaction, the base catalyst, shown in FIG. 2E, generates almost an identical amount of butylenes and propylene. In other words, the selectivity of catalyst components containing MCM-68 zeolite exhibited greater butylenes to propylene selectivity as compared to that catalyst component that contained ZSM-5 zeolite.

Example 4: Activity Related Properties for MCM-68 Zeolite with Varying Levels of Phosphorus Modification Catalyst components with various levels of phosphorus were prepared as described in Example 2 and characterized with respect to their acidity, total surface area, and micropore volume. These properties are believed to be indicative of the catalyst components' performance. The results are summarized in Table 1 below.

TABLE 1

Properties of Steamed MCM-68 Catalyst Components

| Catalyst Component | Total Acidity (mmol/ (g catalyst)) | Total Surface Area ($m^2$/g) | Micropore Volume (cc/g) |
|---|---|---|---|
| MCM-68 | 0.63 | 596 | 0.23 |
| MCM-68/2 wt. % P | 0.44 | 473 | 0.18 |
| MCM-68/4 wt. % P | 0.39 | 347 | 0.13 |
| MCM-68/6 wt. % P | 0.33 | 221 | 0.08 |
| MCM-68_ST | 0.05 | 428 | 0.16 |
| MCM-68/2 wt. % P_ST | 0.10 | 389 | 0.15 |
| MCM-68/4 wt. % P_ST | 0.07 | 296 | 0.11 |
| MCM-68/6 wt. % P_ST | 0.05 | 185 | 0.07 |

The results in Table 1 show that while adding phosphorus to MCM-68 zeolite containing catalyst component does not appear to improve the amount of surface area and/or pore volume retained after steam deactivation, it does help to retain more acid sites (up to a certain amount of added phosphorus). A higher total acidity is believed to be a reflection of higher activity or improved catalytic performance. The results in Table 1 also suggest that there may be a preferred phosphorus content range that provides for improved catalytic performance.

For simplicity of explanation, the embodiments of the methods of this disclosure are depicted and described as a series of acts. However, acts in accordance with this disclosure can occur in various orders and/or concurrently, and with other acts not presented and described herein. Furthermore, not all illustrated acts may be required to implement the methods in accordance with the disclosed subject matter. In addition, those skilled in the art will understand and appreciate that the methods could alternatively be represented as a series of interrelated states via a state diagram or events.

In the foregoing description, numerous specific details are set forth, such as specific materials, dimensions, processes parameters, etc., to provide a thorough understanding of the present invention. The particular features, structures, materials, or characteristics may be combined in any suitable manner in one or more embodiments. The words "example" or "exemplary" are used herein to mean serving as an example, instance, or illustration. Any aspect or design described herein as "example" or "exemplary" is not necessarily to be construed as preferred or advantageous over other aspects or designs. Rather, use of the words "example" or "exemplary" is intended to present concepts in a concrete fashion. As used in this application, the term "or" is intended to mean an inclusive "or" rather than an exclusive "or". That is, unless specified otherwise, or clear from context, "X includes A or B" is intended to mean any of the natural inclusive permutations. That is, if X includes A; X includes B; or X includes both A and B, then "X includes A or B" is satisfied under any of the foregoing instances. Reference throughout this specification to "an embodiment", "certain embodiments", or "one embodiment" means that a particular feature, structure, or characteristic described in connection with the embodiment is included in at least one embodiment. Thus, the appearances of the phrase "an embodiment", "certain embodiments", or "one embodiment" in various places throughout this specification are not necessarily all referring to the same embodiment.

The present disclosure has been described with reference to specific exemplary embodiments thereof. The specification and drawings are, accordingly, to be regarded in an illustrative rather than a restrictive sense. Various modifications of the disclosure in addition to those shown and described herein will become apparent to those skilled in the art and are intended to fall within the scope of the appended claims.

What is claimed is:

1. A process for fluidized catalytic cracking (FCC) of a hydrocarbon feedstock, the process comprising:

contacting, under FCC process conditions, a feedstock comprising at least petroleum crude oil fractions with a first catalyst component comprising a phosphorus stabilized MCM-68 zeolite and a first non-zeolitic matrix, to produce products comprising at least gasoline and olefinic gases.

2. The process of claim 1, wherein the first catalyst component comprises from about 0.5 wt. % to about 10 wt. % phosphorus, based on total weight of the phosphorus stabilized MCM-68 zeolite in the first catalyst component.

3. The process of claim 1, wherein the phosphorus stabilized MCM-68 zeolite has a porous crystalline MSE zeolite structure which contains:

at least one channel system, in which each channel is defined by a 12-membered ring of tetrahedrally coordinated atoms, and at least two further, independent channel systems, in each of which each channel is defined by a 10-membered ring of tetrahedrally coordinated atoms, wherein the number of unique 10-membered ring channels is twice the number of 12-membered ring channels.

4. The process of claim 1, wherein the first catalyst component has a total acidity of about 0.3 mmol/(g catalyst) to about 0.5 mmol/(g catalyst).

5. The process of claim 1, wherein the silicon to aluminum ratio of the phosphorus stabilized MCM-68 zeolite ranges from about 5 to about 60.

6. The process of claim 1, wherein a first butylenes to propylene selectivity ratio, attained from contacting the feedstock with the first catalyst component, is greater than a second butylenes to propylene selectivity ratio, attained from contacting the feedstock with a catalyst component comprising a beta zeolite and/or a ZSM-5 zeolite without phosphorus stabilized MCM-68 zeolite.

7. The process of claim 1, wherein the first catalyst is part of a catalyst composition, and wherein the first catalyst component is present in the catalyst composition in an amount ranging from about 1 wt % to about 25 wt %, based on total weight of the catalyst composition.

8. The process of claim 7, wherein the catalyst composition further comprises a second catalyst component.

9. The process of claim 8, wherein the second catalyst component comprises at least one large pore molecular sieve zeolite having a pore size greater than 7 Angstrom.

10. The process of claim 9, wherein the at least one large pore molecular sieve zeolite is zeolite Y.

11. The process of claim 7, wherein the catalyst composition further comprises at least one additional component that is compositionally different from the second catalyst component and from the first catalyst component.

12. The process of claim 11, wherein the at least one additional component comprises beta zeolite and/or ZSM-5 zeolite and at least one additional non-zeolitic matrix.

13. A catalyst component comprising microspheres including:

phosphorus stabilized MCM-68 zeolite having from about 0.5 wt % to about 10 wt % phosphorus, based on total weight of the phosphorus stabilized MCM-68 zeolite in the catalyst component; and a non-zeolitic matrix comprising one or more of clay, spinel, mullite, kaolin, metakaolin, halloysite, kaolinite, dickite, nacrite, anauxite, silica-thoria, silica-beryllia, and silica-alumina-thoria;

wherein the phosphorus stabilized MCM-68 zeolite is present in the catalyst component from about 1 wt % to about 90 wt %.

14. The catalyst component of claim 13, comprising from about 1 wt % to about 5 wt % phosphorus, based on total weight of the phosphorus stabilized MCM-68 zeolite in the catalyst component.

15. A process for preparing the catalyst component of claim 13, comprising modifying an MCM-68 zeolite with a phosphorus containing compound.

16. A catalyst composition comprising:

first catalyst component microspheres comprising a phosphorus stabilized MCM-68 zeolite having from about 0.5 wt % to about 10 wt % phosphorus, based on total weight of the phosphorus stabilized MCM-68 zeolite in the first catalyst component, and a first non-zeolitic matrix; and second catalyst component microspheres comprising a second zeolite having a pore size greater than 7 angstroms, and a second non-zeolitic matrix;

where the first catalyst component microspheres are present in the catalyst composition in an amount ranging from about 1 wt. % to about 25 wt. %, based on the total weight of the catalyst composition.

17. A process of preparing the catalyst composition of claim 16, comprising combining the first catalyst component with the second catalyst component and optionally with at least one additional component.

* * * * *